United States Patent [19]
Barnoff

[11] Patent Number: 4,748,855
[45] Date of Patent: Jun. 7, 1988

[54] DEVICE FOR IN SITU TESTING OF CONCRETE

[76] Inventor: Robert M. Barnoff, 606 Nimitz Ave., State College, Pa. 16801

[21] Appl. No.: 60,658

[22] Filed: Jun. 11, 1987

[51] Int. Cl.⁴ ............................................. G01N 3/00
[52] U.S. Cl. ......................................... 73/803; 73/84
[58] Field of Search .................. 73/803, 84, 818, 823, 73/825

[56] References Cited

U.S. PATENT DOCUMENTS 3,364,737  1/1968  Comes ................................. 73/84 X
3,457,778  7/1969  Gill et al. ................................ 73/84

Primary Examiner—Jerry W. Myracle
Attorney, Agent, or Firm—Thomas E. Sterling

[57] ABSTRACT

This invention is a testing device for concrete having a cylindrical housing adapted to be inserted in a preformed or drilled cylindrical hole in the concrete. The lower end of the cylindrical housing has one or more openings equi-distantly spaced. These openings have bearing shoes therein which are forced outwardly against the concrete by eccentric cams or a force rod which bears against the bearing shoes. A measuring device connected to the cams or force rod measures the pressure on the shoes and a distance which they extend into the concrete to measure the modulus of elasticity of the concrete from which the ultimate compressive strength of the concrete and other parameters may be determined. The device may be calibrated to yield the ultimate compressive strength directly.

16 Claims, 4 Drawing Sheets

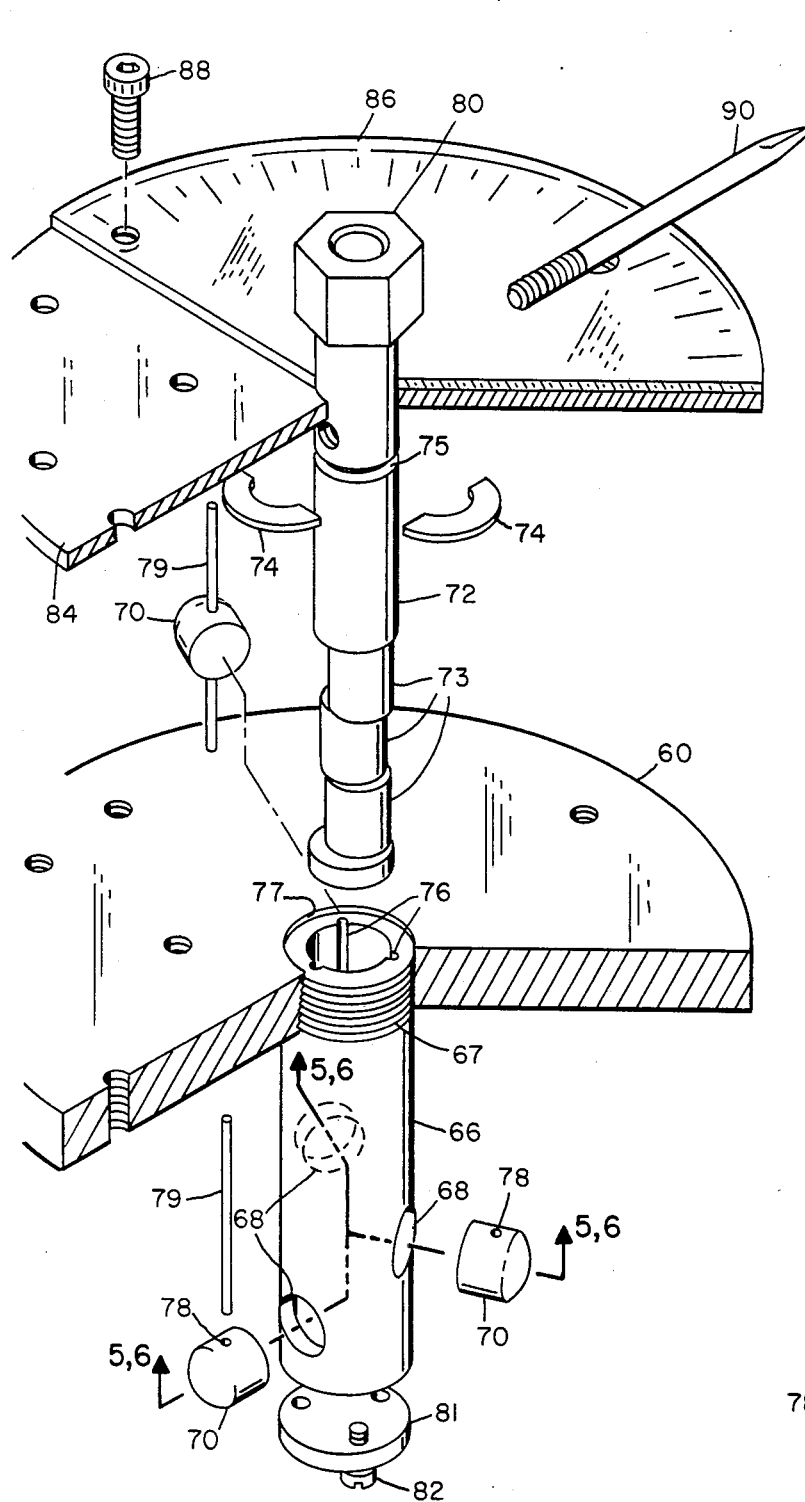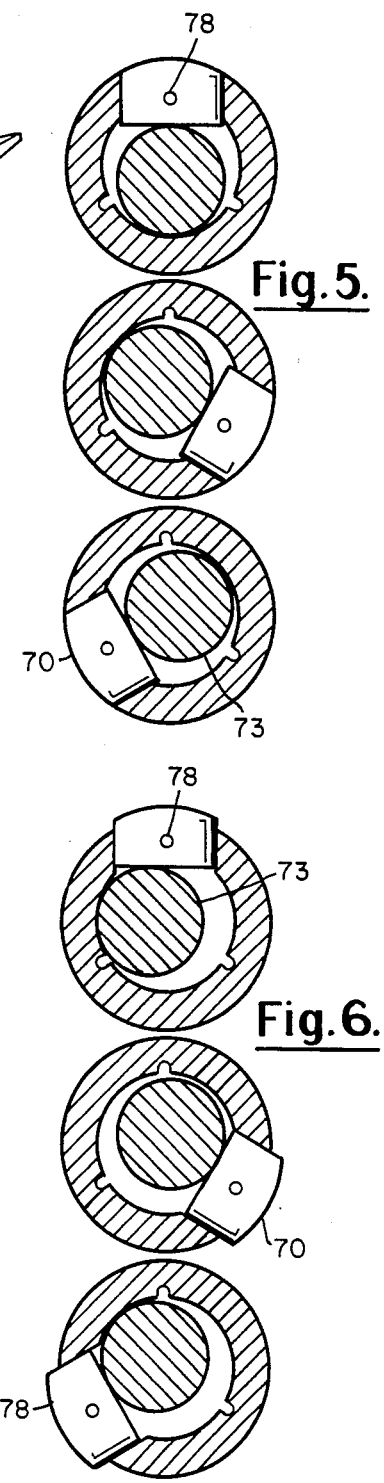
Fig. 4.
Fig. 5.
Fig. 6.

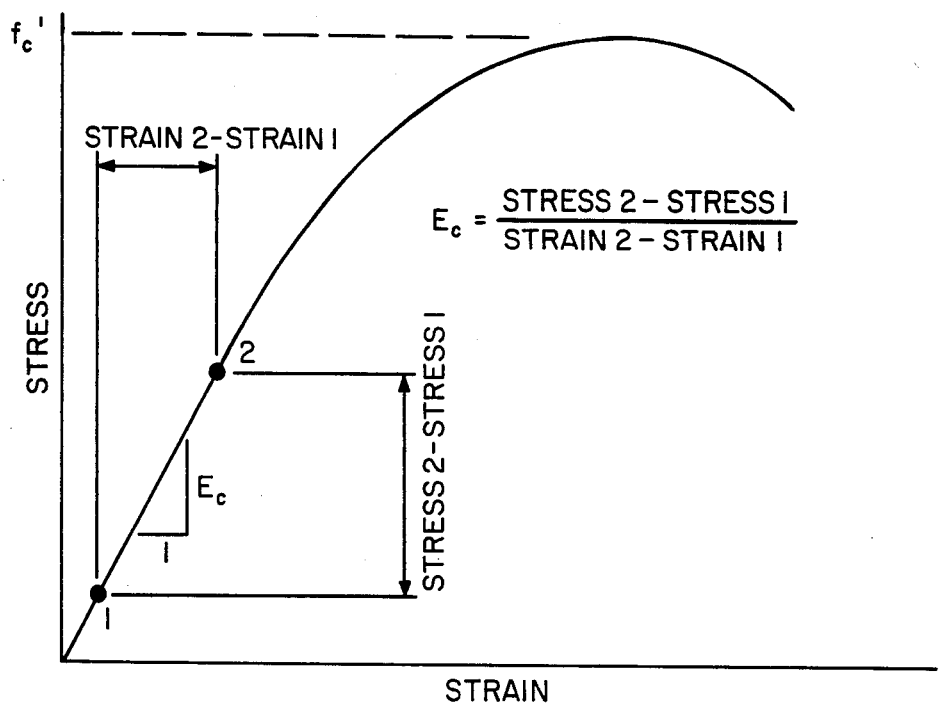
FIGURE 7. - TYPICAL STRESS STRAIN CURVE FOR PORTLAND CEMENT CONCRETE
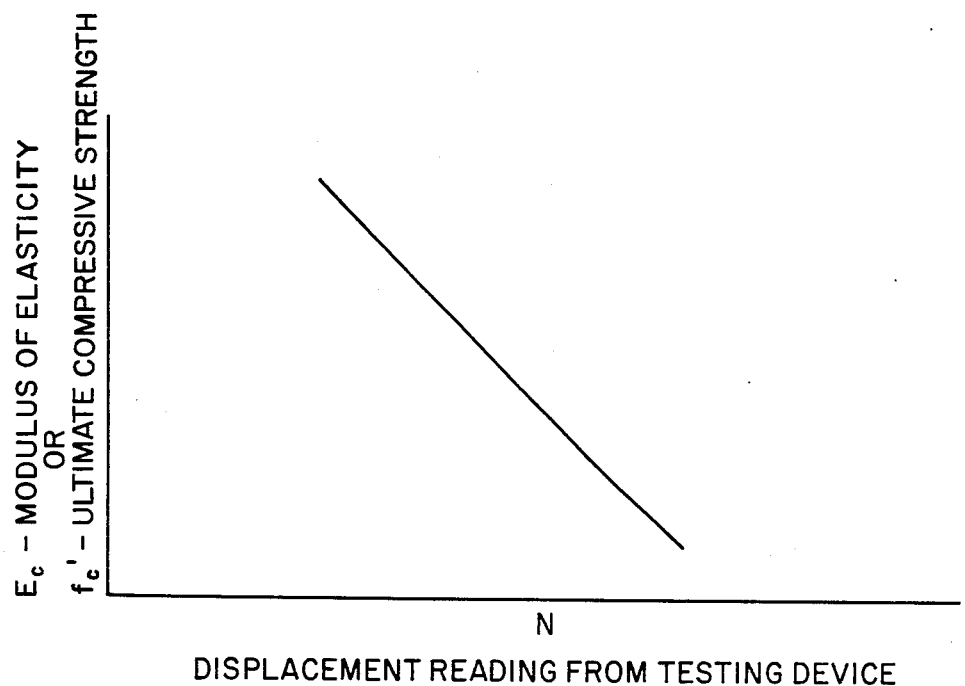
FIGURE 8. TYPICAL CORRELATION CURVE

DEVICE FOR IN SITU TESTING OF CONCRETE

PRIOR ART STATEMENT

The inventor knows of the following United States patents related to this invention: U.S. Pat. No. 3,446,062, 3,595,072. The inventor is not withholding any other known prior art which he considers anticipates this invention.

This invention relates to a mechanism especially designed to determine the strength of portland cement concrete and other similar materials, and more particularly it relates to tests conducted in situ at any time after initial hydration or set of the portland cement concrete.

The present state of the art in concrete testing does not permit random, repeated, non-destructive testing of in situ concrete. Most commonly accepted and widely used test methods are destructive tests which restrict the number of tests to some predetermined number and usually involves concrete which is cast and cured in an environment different from that of the in situ structural concrete. Thus, drastic differences in strength between the test specimen and in situ concrete are possible. This difference in strengths is caused by differences in compaction, mixing, moisture content, and curing conditions. Of particular importance are the differences in curing conditions between the in situ concrete and the test specimen since the shape, thickness, mass and curing temperature all have significant effects on the properties of the concrete. A method in present use involves a device with an enlarged head which is embedded in the plastic concrete during construction. This device is then pulled out with equipment which measures the force required to rupture the concrete in a conical type failure. Thus the rupture modulus strength value is determined. The pull-out test device is in fact an in situ test method, but, only one test can be conducted on each device and this test must be conducted at a predetermined time and location. In contrast, the device of the present inventor hereinafter described permits in situ strength testing at any time after initial hydration of the cement, at any convenient or critical location on the structural member and at any depth below the surface of the concrete.

A reliable method for determining the strength of concrete in structural members is important in the construction industry as well as in the fabrication of precast and prestressed portland cement concrete structural members. Scheduling of work in both of these industries is dependent on the strength of the concrete at early ages. A reliable method for measuring strength is important to determine when forms may be removed or when precast and prestressed members may be prestressed or transported. The strength testing should be reproducible with consistent results that can be evaluated, defined, and incorporated in data useful for design methods and construction specifications.

The objective of this invention is to provide acceptable means and methods of testing concrete in situ at any time after initial set or hardening of the material and at any location on the structure and at any depth in the structural members. In addition this invention permits an infinite number of tests at the same location and at any age, thus the variation in strength with age of concrete can be determined using the same means and method at the same location in the structure. A further advantage of this invention is the ability to evaluate the in situ strength of concrete in existing structures and structural members.

One mode of the present invention consists of a cylindrical housing which is inserted into a preformed or drilled cylindrical hole in the concrete. At the lower end of the cylindrical housing one, two, three or more slots are cut into the wall of the housing. These slots are equally spaced around the perimeter of the housing. Bearing shoes are fitted into the slots in such a manner that the original exterior geometry of the cylindrical housing is maintained. The outside surfaces of the bearing shoes have a curvature that matches the outside radius of the cylindrical housing, while the inside surfaces of the bearing shoes are tapered. This taper matches the taper on the lower end of a force rod which extends through the cylindrical housing and projects from the top of the cylindrical housing. A mechanical or hydraulic device is used to move the force rod into the cylindrical housing, which in turn, causes the bearing shoes to move outward and bear against the concrete around the sides of the hole. Measuring devices are provided to determine the force required to move the force rod, and the magnitude of linear movement of the rod. Thus data may be obtained which relates the force on the bearing shoe with the deformation of the concrete. These data may be correlated with current standard test data for the ultimate compressive strength of concrete or the modulus of elasticity or modulus of rupture of concrete. In order to assure reproducability a predetermined force is applied to the force rod to properly seat the bearing shoes against the concrete before linear measurements are started. Additional force is then applied to the force rod and the load deformation characteristic of the concrete is determined. From the theory of elasticity it can be shown that these load deformation data are directly related to the modulus of elasticity and Poisson's ratio of the concrete.

Several other arrangements of components can be used to apply the necessary force to the force rod. Among these are mechanical devices which produce a given force, and mechanical devices which produce a given displacement. Displacements can be measured with linear voltage displacement transducers, micrometers or any other linear measuring device. The magnitude of force in the force rod can be measured by any mechanical, hydraulic or electrical device which can accurately measure the total force in the rod.

A second mode for applying force to the bearing shoes is the use of a shaft with eccentric cams, in conjunction with bearing shoes with a flat or slightly curved contact surface with the eccentric cams. When a torque is applied to the shaft the bearing shoes are forced outward and produces a bearing pressure between the shoes and concrete. As torque is applied to the shaft, the rotational displacement is measured, and a correlation can be developed relating the torque-rotation values to the mechanical properties of the concrete.

Although the descriptions used in this patent are for measuring the strength of portland cement concrete, the device can be used to measure the strength properties of a wide variety of elastic and semi-elastic materials. These materials include but are not limited to: mortars, bricks, asphaltic concretes, wood, rock, gypsum, plastics, polymers, etc.

Portland cement concrete is used extensively in the construction of buildings, bridges, pavements, foundations, tunnels and many other structures. Specifications for the design and construction of major structures use the ultimate compressive strength of the material at the age of 28 days as the principal design parameter and as a means of quality control in the production of the material. This 28 day strength is measured by loading a 6 inch diameter by 12 inch high cylinder with an axial compressive load until the cylinder fails. The load which causes failure is divided by the cross sectional area of the cylinder to obtain the ultimate compressive strength which is called $f_c'$. Details of the testing procedure may be found in the American Society for Testing and Materials standard C39-86, "Standard Test Method for Compressive Strength of Cylindrical Concrete Specimens".

Another important parameter used in the design of concrete structures is the modulus of elasticity, which is also called the chord modulus. The modulus of elasticity is obtained from a 6 inch diameter by 12 inch long cylinder by measuring the shortening of the cylinder as it is subjected to a compressive stress. The change in length of the concrete at given stress levels is divided by the length over which it is measured to obtain the strain. A plot of the stress vs. strain for a typical concrete is shown in FIG. 7. For values of stress which are less than one half the ultimate compressive stress, the curve is approximately a straight line. Thus, only two points (two measurements of stress and strain) are required to define this portion of the curve. The points 1 and 2 shown on the curve illustrate the two measured points. From these two points, the modulus of elasticity can be obtained by finding the slope of the curve by dividing the stress by the strain. The formula: $E_c$=Stress/-Strain=(Stress 2-Stress 1) (Strain 2-Strain 1) may be used. Details for obtaining the data to plot the stress strain curve and to measure the modulus of elasticity may be found in the American Society for Testing and Materials standard C469-83, "Standard Test Method for Static Modulus of Elasticity and Poisson's Ratio of Concrete in Compression".

The relationship between the modulus of elasticity and the ultimate compressive strength of concrete is given by the following formula from "Building Code Requirements for Reinforced Concrete Structures (ACI 318-83)" which is published by the American Concrete Institute:

$$E_c = w_c^{1.5} 33 f_c'$$

Where $w_c$ is the unit weight of the concrete.

In order to measure the strength of concrete using the device described in this invention, a correlation is established between the measurements taken by the device and the modulus of elasticity of the concrete. This correlation may be expressed by a curve as shown in FIG. 8, where N is the difference in displacement readings taken using two predetermined force values. The operator of the device takes two readings of the displacement at the predetermined force values, and obtains N by finding the difference between the two readings. After obtaining the N value, the modulus of elasticity and strength of the concrete may be obtained from the correlation curves or tables that are developed for the material being evaluated.

An object of this invention is to provide a device and method of testing hardened concrete in situ at any location and depth in a structural member.

Another object of this invention is to provide a testing device for concrete utilizing a downwardly thrust force rod activating outwardly thrust bearing shoes.

Still another object of this invention is to provide a concrete testing device operable in a preformed hole in concrete.

Still another object of this invention is to provide a concrete testing device utilizing a shaft with eccentric cams in conjunction with outwardly thrust bearing shoes.

Yet another object of this invention is to provide a concrete testing device powered by hydraulic means.

Another object of this invention is to provide a concrete testing device operable by hand means.

Yet another object of this invention is to provide a testing device which may be used to test mortars, bricks, asphaltic concretes, wood, rock, gypsum, plastics, polymers or the like.

Still another object of this invention is to provide a testing device which may utilize hydraulic, electric, electronic and mechanical means for measuring force and bearing shoes displacement.

Yet another object of this invention is to provide a process for determining the modulus of elasticity, ultimate compressive strength and Poisson's ratio of concrete in compression.

Yet another object of this invention is to provide a process of determining certain parameters of concrete utilizing a stress strain curve and correlation curve graphs.

These and other objects of the invention may be seen by reference to the following drawings, specification and claims.

FIG. 4, is a third dimensional view of the device of FIG. 3, in disassembled form.

FIG. 5, is a view taken along line 5 of FIG. 4, showing a cross-section of the cams of the device with the bearing shoes in a nonextended position.

FIG. 6, is a view taken along line 6 of FIG. 4, showing a cross-section of the cams of the device with the bearing shoes in an extended position.

FIG. 7, is a graph of a typical stress strain curve for portland cement concrete.

FIG. 8, is a typical correlation curve for determining the properties of portland cement concrete using the device.

Figures 1, 2:
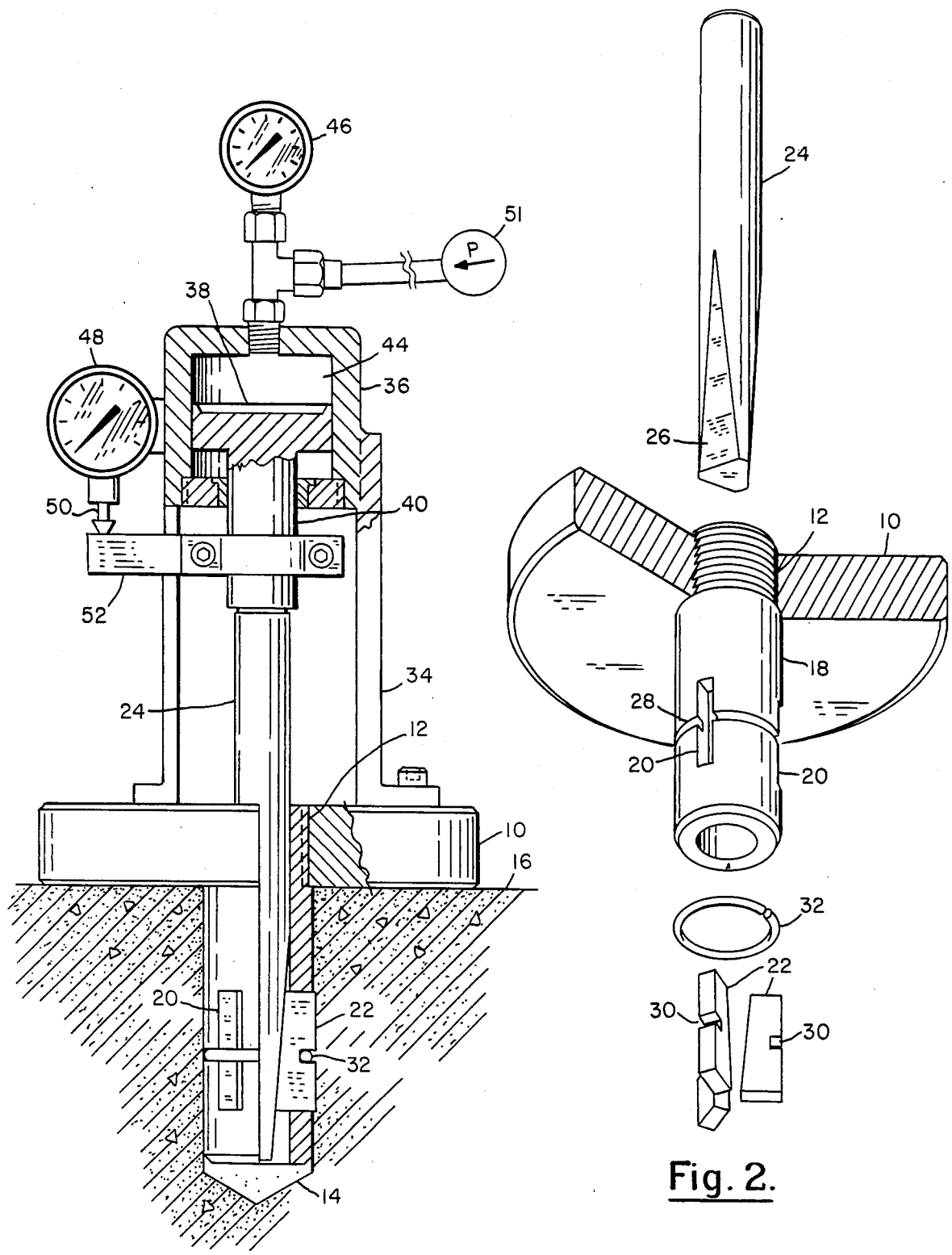
FIG. 1, is a side view of a first mode of the device, partially in section, positioned in a preformed hole in concrete.
FIG. 2, is a third dimensional view of the device of FIG. 1, in disassembled form showing the force rod assembly and the cylindrical housing assembly.
Figure 3:
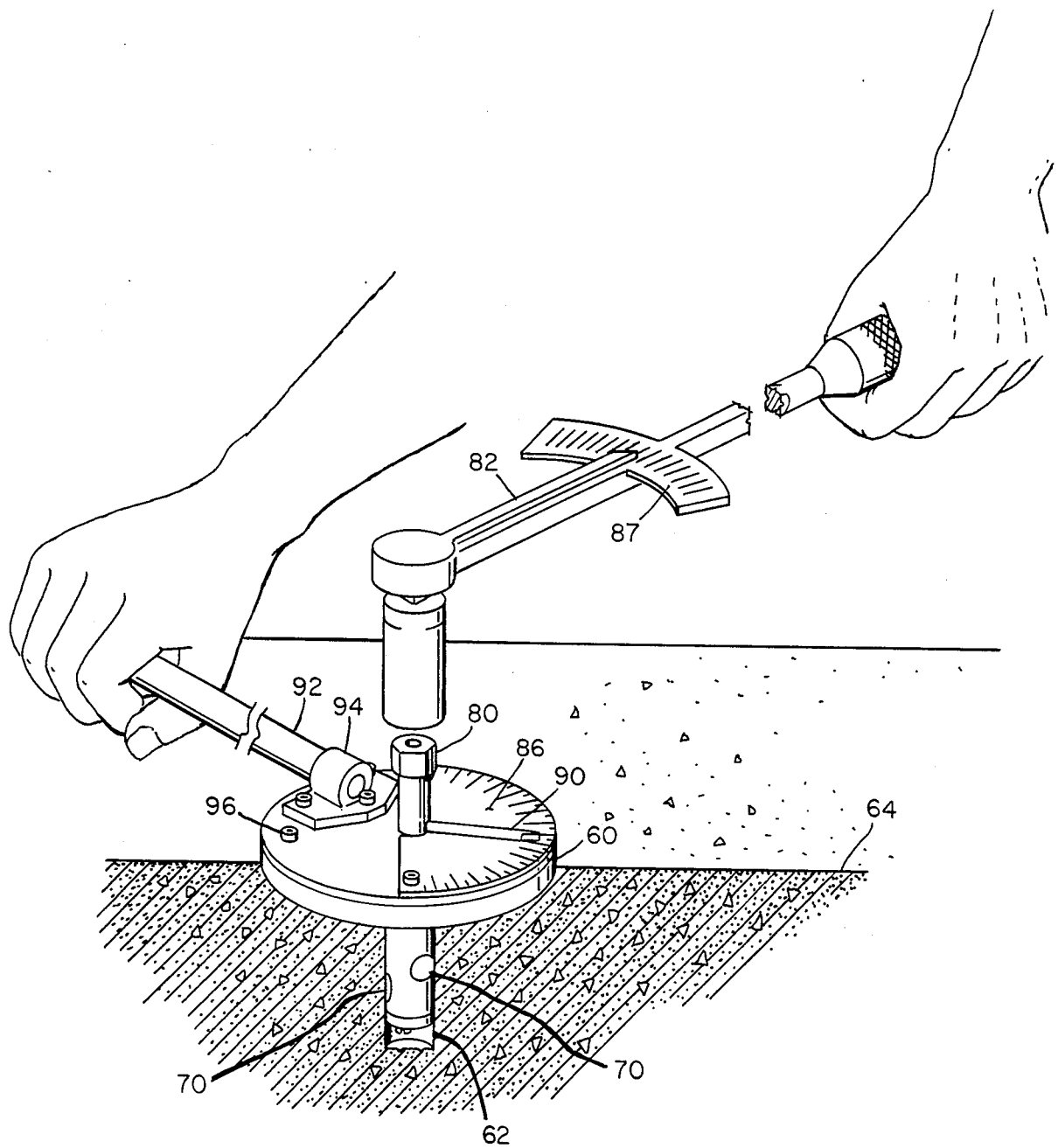
FIG. 3, is a third dimensional view of a second mode of the device positioned in a preformed hole in concrete.

Referring to the drawings and in particular to FIGS. 1 and 2, 10 represents a cylindrical base plate having a threaded hole 12 in the central portion therein. Hole 12 is positioned directly above a preformed hole 14 in concrete 16. A hollow cylindrical housing 18 is thread attached to threaded hole 12 and extends within the preformed hole 14. The lower portion of cylindrical housing 18 has three vertical slots 20 therein equidistantly positioned from one another about the circumference. Tapered bearing shoes 22 are slidably positioned within slots 20 with end tapered portions within hollow cylindrical housing 18. A force rod 24 having three tapered end portions 26 extends through hollow cylindrical housing 18 to slidably contact the matching taper of bearing shoes 22. It may be seen that by pressing force rod 24 within cylindrical housing 18, bearing shoes 22 will be forced outward by tapered end portion 26 of force rod 24. Although three slots 20 and bearing shoes 22 are described, it should be understood that one or more slots and bearing shoes may be utilized without departing from the spirit of this device. A circumferential slot 28 extends about cylindrical housing 18. Matching slots 30 in bearing shoes 22 accommodate a retaining spring 32 which extends around and retains the bearing shoes within slots 20.

A cylindrical support element 34 is bolt attached to base plate 10 and is coupled to hydraulic cylinder 36 at the upper portion thereof. Hydraulic cylinder 36 contains hydraulic piston 38 with attached piston rod 40 which contacts the upper portion of force rod 24. A hydraulic line 42 is in communication with the internal portion of hydraulic cylinder 36 and supplies hydraulic fluid 44 to within hydraulic cylinder 36. Hydraulic line 42 has a hydraulic fluid pressure measuring device 46 attached thereto which indicates the hydraulic pressure within hydraulic cylinder 36 and the total force exerted on force rod 24. Pressure measuring device 46 is connected to a hydraulic pump 51. A distance measuring indicator 48 is attached to hydraulic cylinder 36. An indicator arm 50 is in contact with rod clamp 52 secured to piston rod 40. Thus when piston rod 40 and force rod 24 move, indicator 48 displays the distance that each has traversed.

In operation, force rod 24 is placed within preformed hole 14 in concrete 16. Hydraulic fluid 44 is pumped by hydraulic pump 51 into hydraulic cylinder 36 forcing hydraulic piston 38 and piston rod 40 downwardly against force rod 24. Tapered end portion 26 of force rod 24 bears against taper bearing shoes 22 forcing them outward against the concrete 16. A distance reading is taken on indicator 48, and an additional hydraulic fluid 44 introduced into hydraulic cylinder 36 forcing force rod 24 downward and shoes 22 outward. A reading is again taken on indicator 48 and on hydraulic fluid measuring device 46. From these two readings, a calculation may be made.

A modification of this device may be seen by reference to FIGS. 3, 4, 5 and 6. This modification utilizes camming action to force bearing shoes into the concrete. In this modification base plate 60 is positioned above hole 62 in the concrete 64. A hollow cylinder 66 is attached to base plate 60 by screw means 67. Hollow cylinder 66 extends into hole 62 and at the bottom portion thereof has three shoe holes 68 extending through hollow cylinder 66. Shoe holes 68 are circular and are positioned equi-distant from one another, each being about 120 degrees from the other. In addition they are positioned a vertical distance from one another on hollow cylinder 66. cylindrical bearing shoes 70 are slidably positioned within shoe holes 68 so that they may easily slide in and out.

A cam shaft 72 extends within hollow cylinder 66 and protrudes above the base plate 60. Split rings 74 are inserted in circumferential ring slot 75 in the upper portion of cam shaft 72. Split rings 74 are then positioned in a ring recess 77 in the upper surface of base plate 60. Split rings 74 support cam shaft 72 and allow it to rotate. The lower end portion of cam shaft 72 has three circular eccentric cams 73 thereon adapted to contact the three bearing shoes 70. The rotating of cam shaft 72 within hollow cylinder 66 will cause the cams on cam shaft 72 to bear against bearing shoes 70 and force them outward from hollow cylinder 66. The cams are so geared that all three bearing shoes 70 will proceed outward in unison. This can be more clearly seen by referring to FIGS. 5 and 6. Three longitudinal spring grooves 76 extend within hollow cylinder 66 to the shoe holes 68 where they are met by a spring hole 78 extending through each bearing shoe 70. A retractor spring 79 extends within grooves 76 through spring hole 78 of each bearing shoe. This spring 79 is so biased that it will withdraw the bearing shoes 70 into hollow cylinder 66 after they have been pressed outward by cams 73. A cylinder cover 81 is screw attached to the bottom portion of hollow cylinder 66 by means of screws 83.

The upper end of cam shaft 72 has a hexagonal nut 80 attached thereto which is adapted to fit upon a calibrated torque wrench 82 with a scale 87. A circular indicator base 84 is attached to the upper portion of base plate 60. A circular indicator 86 is positioned upon the indicator base 84. Both are attached to base plate 60 by means of screw 88. A pointer 90 having a threaded end portion engages threads in cam shaft 72 above indicator 86 so that the pointer 90 is readable against the markings on indicator 86. A handle 92 is attached to handle bracket 94 which is attached to base plate 60 by means of screws 96.

In operation, the hollow cylinder 66 is placed in hole 62, torque wrench 82 placed on hexagonal nut 80. The operator then grasps the handle 92 and the torque wrench 82, applying pressure in a rotary manner so that bearing shoes 70 bear against the concrete 64. A reading of pointer 90 upon indicator 86 is then taken and additional pressure is applied causing the bearing shoes 70 to bear strongly against concrete 64. A reading of the scale 87 is then taken and a reading of the pointer 90 on the indicator 86 which gives the distance that the bearing shoes 70 have pressed into the concrete 64. From this reading and other similar ones, computations can be made relative to the strength of the concrete.

EXAMPLE

A hole is preformed or drilled into the concrete at the location where the strength of the material is to be evaluated. The diameter of the hole is just large enough to permit the cylinder of the torque testing device to be inserted without force. After the testing device is inserted, a calibrated torque wrench or other mechanism is used to apply a small predetermined torque to the shaft using the hexagon head on the top of the shaft, or by some other means. After the initial torque is applied the initial rotation of the shaft is obtained using the pointer and the calibrated marks on the base plate. The torque is then increased to a second predetermined value by using the torque wrench and simultaneously holding the handle to prevent rotation of the base plate. After application of the second predetermined torque, the rotation of the shaft is observed as before. The difference between the initial and final shaft rotation is obtained and designated as a value called N. This value is used with a calibration curve or table to obtain the modulus of elasticity or ultimate compressive strength. See FIGS. 7 and 8.

While the invention has been described by means of a specific example and in a specific embodiment, we do not wish to be limited thereto, for obvious modifications will occur to those skilled in the art without departing from the spirit and scope of the invention.

I claim:

1. A concrete testing device adapted to test within a preformed or drilled hole in concrete, comprising in combination:

a base plate positioned upon said preformed hole;

a hollow housing attached to said base plate and extending into said preformed hole, said hollow housing having a slot therethrough;

a bearing shoe slidably positioned within said slot;

a tapered surface on said bearing shoe;

a force rod within said hollow housing;

a tapered element upon said force rod in contact with said tapered surface on said bearing shoe;

hydraulic cylinder means attached to said hollow housing and to said force rod;

pressure measuring means in communication with said hydraulic cylinder means;

a distance measuring indicator in communication with said force rod.

2. The combination as claimed in claim 1, in which said hydraulic cylinder means is comprised of, in combination:

a hydraulic cylinder;

a moving piston within said hydraulic cylinder, said piston attached to said force rod;

a hydraulic fluid source connected to said hydraulic cylinder.

3. The combination as claimed in claim 2, in which said bearing shoe has a spring slot therein;

a retractor spring positioned within said spring slot.

4. The combination as claimed in claim 3, in which said pressure measuring means is comprised of, in combination:

a hydraulic pressure gauge in communication with said hydraulic-fluid source.

5. The combination as claimed in claim 4, in which said distance measuring indicator is comprised of, in combination:

a distance measuring gauge attached to said hydraulic cylinder;

an indicator arm attached to said pressure measuring means and in communication with said force rod.

6. The combination as claimed in claim 5, in which said hollow housing contains three bearing shoes equidistantly positioned from one another and said force rod has three equi-distant tapers thereon in contact with said three bearing shoes.

7. A testing device for use within a preformed or drilled hole in concrete, comprising in combination:

a base plate with a hole therethrough positioned adjacent to said preformed hole;

a hollow housing attached to said base plate extending within said preformed hole, said hollow housing having a shoe hole therethrough;

a bearing shoe slidably positioned within said shoe hole;

a cam shaft rotatably positioned within said hollow housing;

an eccentric cam positioned on said cam shaft, said cam in contact with said bearing shoe;

torque measuring means attached to said cam shaft;

angular measuring means attached to said cam shaft.

8. The combination as claimed in claim 7, in hich said torque measuring means is comprised of, in combination:

a torque wrench attached to said cam shaft adapted to indicate torque applied to sa1d cam shaft;

a handle attached, to said base plate adapted to be hand held.

9. The combination as claimed in claim 8, in which said angle measuring means is comprised of, in combination:

an indicator plate attached to said base plate;

a pointer attached to said cam shaft and readably positioned upon said indicator plate.

10. The combination as claimed in claim 9, in which said bearing shoe has a retracting spring connected thereto adapted to withdraw said bearing shoe within said hollow housing.

11. The combination as claimed in claim 10, in which said cam shaft has three eccentric cams attached thereto, said hollow housing has three bearing shoes slidably positioned therethrough in contact with said three eccentric cams.

12. The combination as claimed in claim 11, in which said torque wrench is removably attached to said cam shaft.

13. The combination as claimed in claim 12, in which said hollow housing has a cover attached to the end portion thereof.

14. The combination as claimed in claim 13, in which said hollow housing has three longitudinal grooves on the outside portion thereof;

said bearing shoes have three holes therethrough adjacent to said longitudinal grooves;

three retracting springs positioned within said longitudinal grooves and extending through said three holes and said bearing shoes.

15. The combination as claimed in claim 14, in which said cam shaft has a circumferential ring slot therein;

a split ring within said ring slot;

said base plate has a ring recess therein;

said split ring positioned within said ring recess.

16. A device for determining the mechanical properties of portland cement concrete and similar materials adapted to the utilization of a preformed or drilled hole in concrete, said device comprising of, in combination:

a cylinder, having a bearing shoe hole therethrough;

a cam shaft rotatably positioned within said cylinder;

an eccentric cam positioned on said cam shaft;

a bearing cam positioned within said bearing shoe hole and in contact with said eccentric cam;

torque measuring means attached to said cam shaft;

angular measuring means attached to said cam shaft.

* * * * *